United States Patent [19]
Clayton

[11] Patent Number: 5,968,917
[45] Date of Patent: Oct. 19, 1999

[54] COMPOSITION CONTAINING DIOSGENIN

[75] Inventor: Paul Rodney Clayton, London, United Kingdom

[73] Assignee: The Boots Company PLC, Nottingham, United Kingdom

[21] Appl. No.: 09/101,436

[22] PCT Filed: Jan. 10, 1997

[86] PCT No.: PCT/EP97/00166

§ 371 Date: Jul. 13, 1998

§ 102(e) Date: Jul. 13, 1998

[87] PCT Pub. No.: WO97/25049

PCT Pub. Date: Jul. 17, 1997

[30] Foreign Application Priority Data

Jan. 12, 1996 [GB] United Kingdom .................. 9600604

[51] Int. Cl.$^6$ .................. A61K 31/705; A61K 31/56; A61K 31/59; A61K 31/12
[52] U.S. Cl. .................. 514/167; 514/26; 514/171; 514/178; 514/681
[58] Field of Search .................. 514/167, 178, 514/26, 681, 171

*Primary Examiner*—Theodore J. Criares
*Attorney, Agent, or Firm*—Nikaido, Marmelstein, Murray & Oram LLP

[57] ABSTRACT

Method of treating osteoporosis according to the present invention comprises the administration to a subject in need thereof a therapeutically effective amount of diosgenin, a therapeutically effective amount of vitamin K and a therapeutically effective amount of vitamin D.

4 Claims, No Drawings

COMPOSITION CONTAINING DIOSGENIN

This application is a 371 of PCT/EP97/00166 filed Jan. 10, 1997.

The present invention relates to the prevention and treatment of osteoporosis and to compositions for use in such prevention or treatment.

Compositions for the prevention and treatment of osteoporosis according to the present invention comprise a therapeutically effective amount of diosgenin, a therapeutically effective amount of vitamin K and a therapeutically effective amount of vitamin D. Optionally the composition also contains a therapeutically effective amount of vitamin B6 and/or vitamin A.

Method of preventing or treating osteoporosis according to the present invention comprises the administration to a subject in need thereof a therapeutically effective amount of diosgenin, a therapeutically effective amount of vitamin K and a therapeutically effective amount of vitamin D. Optionally the method of the present invention also comprises the administration of a therapeutically effective amount of vitamin B6 and/or vitamin A. The diosgenin, vitamin K, vitamin D and optional vitamins B6 and A may be administered simultaneously or sequentially. For simultaneous administration the components may be combined into a single dosage form or may be formulated into several dosage forms which are intended to be taken at the same time.

Diosgenin [(25R)-spirost-5-en-3β-ol] used in the compositions and method of the present invention may be used in a chemically pure form which may be isolated from natural sources (eg from yams), may be prepared by chemical modification of saponins obtained from natural sources or may be prepared synthetically. Alternatively, an extract obtained from a natural source which is rich in diosgenin or a precursor thereto may be used. A suitable source would be an extract of yam. The amount of diosgenin to be administered per day is in the range 100 to 2000 mg preferably 150 to 1200 mg most preferably 300 to 1200 mg. This amount may be administered in a single dose or in more than one dose which may be taken at different times throughout the day.

The Term "Vitamin K" as used herein is intended to cover vitamin K in any of its forms (ie vitamin K1, vitamin K2, vitamin K3, vitamin K4, vitamin K5, vitamin K6 and vitamin K7) or any precursor or analogue to any of these vitamins (such as the naphthaquinones) which would give rise to vitamin K -like activity after administration. Preferred vitamin K components are provided by vitamin K1 and/or vitamin K2. The amount of vitamin K to be administered per day is in the range 5 to 5000 μg, preferably 10 to 200 μg. This amount may be administered in a single dose or in more than one dose which may be taken at different times throughout the day.

The term "Vitamin D" as used herein is intended to cover vitamin D in any of its forms (ie vitamin D1 vitamin D2, vitamin D3 or vitamin D4) or any precursor or analogue to any of these vitamins which would give rise to vitamin D-like activity after administration. The preferred form of vitamin D is vitamin D3. The amount of vitamin D to be administered per day is in the range 5 to 5000 μg preferably 10 to 100 μg. This amount may be administered in a single dose or in more than one dose which may be taken at different times throughout the day.

The term "Vitamin B6" as used herein is intended to cover pyridoxine hydrochloride or any other of the vitamins of the B6 complex (ie codecarboxyiase, pyridoxal hydrochloride or pyridoxamine dihydrochloride) or any precursors or analogues thereof which would give rise to vitamin B6-like activity. The amount of vitamin B6 to be administered per day is in the range 1 to 1000 mg, preferably 5 to 100 mg. This amount may be administered in a single dose or in more than one dose which may be taken at different times throughout the day.

The amount of vitamin A to be administered per day is in the range 1 to 4 mg. This amount may be administered in a single dose or in more than one dose which may be taken at different times during the day.

The pharmaceutical compositions of the present invention may be administered as oral dosage forms and may be solid dosage forms eg tablets, capsules, lozenges, chewable tablets or capsules or may be liquid dosage forms eg solutions, suspensions, dispersions or syrups. A preferred pharmaceutical composition is a soft-gel capsule in which the active ingredients are dissolved or dispersed in a liquid non-aqueous centre. Alternatively, the compositions of the present invention may be formulated so that the active materials are administered transdermally. Examples of suitable transdermal dosage forms are creams and gels containing the active materials or patches which may be adhesively attached to the skin and which contain a reservoir of the active material optionally in combination with a penetration enhancer or other suitable excipients.

These oral and transdermal dosage forms may be prepared by methods which are well-known to those skilled in the art.

The preferred soft gel capsules may be prepared by dissolving or suspending the active ingredients and any excipients or other desirable formulation aids in an oily medium which is then encapsulated in the soft gel capsule.

The efficacy of the compositions of the present invention and the effectiveness of the method of the present invention has been shown by means of clinical trials. In one such trial, post-menopausal female volunteers received the compositions of the present invention containing diosgenin and vitamins K, D and B6 for a period of 84 days. All subjects were given the same amounts of vitamins K, D and B6 (120 μg of vitamin K1, 20 μg of vitamin D3 and 10 mg of vitamin B6) but individual subjects received daily doses of diosgenin of 300 or 600 mg per day. The dose of diosgenin given to a particular subject remained constant throughout the trial period. Analysis of blood and urine samples taken at the start, midpoint and end of the trial showed that there were significant increases in the two most sensitive biochemical markers of bone formation, namely alkaline phosphatase activity and osteocalcin levels.

In a second such trial, which is conducted on the double blind placebo controlled principle in which neither the subjects nor the physician are aware of whether the subject is receiving active material or placebo, the biochemical parameters of bone metabolism are measured in two groups of post-menopausal women for a period of 18 months. One group receives the composition of the present invention and the other group receives placebo. Bone mass is also measured at appropriate points in the trial.

I claim:

1. Compositions for the prevention and treatment of osteoporosis comprising a therapeutically effective amount of diosgenin, a therapeutically effective amount of vitamin K and a therapeutically effective amount of vitamin D.

2. Compositions as claimed in claim 1 which also contain a therapeutically effective amount of vitamin B6 and/or vitamin A.

3. A method of preventing or treating osteoporosis comprising the administration to a subject in need thereof a therapeutically effective amount of diosgenin, a therapeutically effective amount of vitamin K and a therapeutically effective amount of vitamin D.

4. The method according to claim 3 which also comprises the administration of a therapeutically effective amount of vitamin B6 and/or vitamin A.

* * * * *